US012805759B2

(12) United States Patent
Riggs et al.

(10) Patent No.: US 12,805,759 B2
(45) Date of Patent: Nov. 24, 2026

(54) WEARABLE DEVICES AND SYSTEMS FOR MONITORING AUDITORY BIOMARKERS AND RELATED METHODS

(71) Applicant: OHIO STATE INNOVATION FOUNDATION, Columbus, OH (US)

(72) Inventors: William Riggs, Columbus, OH (US); Oliver F. Adunka, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 462 days.

(21) Appl. No.: 18/276,986

(22) PCT Filed: Feb. 11, 2022

(86) PCT No.: PCT/US2022/016085
§ 371 (c)(1),
(2) Date: Aug. 11, 2023

(87) PCT Pub. No.: WO2022/174018
PCT Pub. Date: Aug. 18, 2022

(65) Prior Publication Data

US 2024/0115168 A1 Apr. 11, 2024

Related U.S. Application Data

(60) Provisional application No. 63/148,191, filed on Feb. 11, 2021.

(51) Int. Cl.
*A61B 5/12* (2006.01)
*A61B 5/00* (2006.01)
(Continued)

(52) U.S. Cl.
CPC ................ *A61B 5/125* (2013.01); *A61B 5/01* (2013.01); *A61B 5/254* (2021.01); *A61B 5/256* (2021.01);
(Continued)

(58) Field of Classification Search
CPC ........... A61B 5/125; A61B 5/01; A61B 5/254; A61B 5/256; A61B 5/291; A61B 5/372;
(Continued)

(56) References Cited

U.S. PATENT DOCUMENTS 4,462,411 A 7/1984 Rickards
5,954,667 A 9/1999 Finkenzeller et al.
(Continued)

OTHER PUBLICATIONS

International Search Report an Written Opinion in Application No. PCT/US2022/016085, mailed May 11, 2022, 9 pages.

*Primary Examiner* — Adam J Eiseman
*Assistant Examiner* — Lucy Eppert
(74) *Attorney, Agent, or Firm* — Meunier Carlin & Curfman LLC

(57) ABSTRACT

Example portable devices, systems, and methods for monitoring hearing sensitivity are described herein. An example device includes a wearable member, a stimulator, and a sensor that includes a plurality of electrodes. The stimulator and the sensor are integrated into the wearable member. Additionally, the device includes a controller operably coupled to the stimulator and the sensor, and the controller is configured to deliver a stimulation signal to a subject's ear using the stimulator, and receive an electrophysiological response signal of the subject in response to the stimulation signal. The electrophysiological response signal is recorded by the sensor. Optionally, the controller is integrated into the wearable member.

27 Claims, 6 Drawing Sheets

(51) Int. Cl.

| | |
|---|---|
| ***A61B 5/01*** | (2006.01) |
| ***A61B 5/254*** | (2021.01) |
| ***A61B 5/256*** | (2021.01) |
| ***A61B 5/291*** | (2021.01) |
| ***A61B 5/372*** | (2021.01) |
| ***A61B 5/38*** | (2021.01) |
| ***A61B 5/384*** | (2021.01) |

(52) U.S. Cl.
CPC .............. *A61B 5/291* (2021.01); *A61B 5/372* (2021.01); *A61B 5/38* (2021.01); *A61B 5/384* (2021.01); *A61B 5/6803* (2013.01); *A61B 5/746* (2013.01)

(58) Field of Classification Search
CPC ......... A61B 5/38; A61B 5/384; A61B 5/6803; A61B 5/746; A61B 5/294; A61B 5/374; A61B 5/7253; A61B 5/7275
See application file for complete search history.

(56) References Cited

U.S. PATENT DOCUMENTS

| | | | | |
|---|---|---|---|---|
| 6,343,230 | B1 | 1/2002 | Smits et al. | |
| 2012/0197153 | A1* | 8/2012 | Kraus ...................... | A61B 5/38 600/545 |
| 2013/0085346 | A1 | 4/2013 | Lin et al. | |
| 2016/0242699 | A1* | 8/2016 | Das ...................... | A61B 5/7264 |
| 2017/0340855 | A1* | 11/2017 | Soulet De Brugiere .................... | A61B 5/6814 |
| 2018/0056083 | A1* | 3/2018 | Jin ....................... | A61B 5/4836 |
| 2018/0279952 | A1* | 10/2018 | Orron ................ | A61B 5/02055 |
| 2019/0246982 | A1* | 8/2019 | Mackellar ............. | A61B 5/291 |
| 2020/0345243 | A1 | 11/2020 | LeBoeuf et al. | |
| 2021/0314692 | A1* | 10/2021 | Campbell ............ | H04R 1/1008 |
| 2023/0029042 | A1* | 1/2023 | Facteau ............. | A61B 5/14551 |

* cited by examiner

WEARABLE DEVICES AND SYSTEMS FOR MONITORING AUDITORY BIOMARKERS AND RELATED METHODS

CROSS-REFERENCE TO RELATED APPLICATIONS

This application is a United States National Phase Patent Application of International Patent Application Number PCT/US2022/016085, filed on Feb. 11, 2022, which claims the benefit of U.S. provisional patent application No. 63/148,191, filed on Feb. 11, 2021, and titled "WEARABLE DEVICES AND SYSTEMS FOR MONITORING AUDITORY BIOMARKERS AND RELATED METHODS," the disclosure of which are expressly incorporated herein by reference in their entireties.

BACKGROUND

Over 1.1 billion people are at risk for hearing loss due to unsafe sound levels as a result of personal use of portable music devices (e.g. smart devices). Furthermore, among teenagers and young adults aged 12-35 years, nearly 50% are exposed to unsafe levels of sound from the use of personal audio devices. Unaddressed hearing loss poses an annual global cost of $750 billion (WHO 2020). Interventions to prevent hearing loss are cost-effective and can bring great benefit to individuals such as the ability to hear and communicate with loved ones. Despite a large population being at risk for acquired hearing loss due to excessive noise exposure, there is currently a lack of an available objective technique to measure and monitor hearing sensitivity for the general population without going to a licensed professional such as an audiologist. Thus, methods and/or devices for detecting the early moments of hearing loss and allowing for change in personal listening habits to better protect hearing are nonexistent.

SUMMARY

An example portable device for monitoring hearing sensitivity is described herein. The device includes a wearable member, a stimulator, and a sensor that includes a plurality of electrodes. The stimulator and the sensor are integrated into the wearable member. Additionally, the device includes a controller operably coupled to the stimulator and the sensor, and the controller is configured to deliver a stimulation signal to a subject's ear using the stimulator, and receive an electrophysiological response signal of the subject in response to the stimulation signal. The electrophysiological response signal is recorded by the sensor. Optionally, the controller is integrated into the wearable member.

Ire some implementations, the stimulator is an electroacoustic transducer and the stimulation signal is an acoustic stimulation signal. The controller is configured to actuate the electroacoustic transducer to deliver the acoustic stimulation signal to the subject's ear. Additionally, the acoustic stimulation signal is configured to activate the subject's inner ear.

In some implementations, the stimulator is a bone oscillator and the stimulation signal is a bone conduction stimulation. The controller is configured to actuate the bone oscillator to the deliver the bone conduction stimulation to the subject's ear. Additionally, the bone conduction stimulation is configured to activate the subject's inner ear.

In some implementations, the wearable member is configured to be worn around a portion of the subject's head. For example, the wearable member includes at least one ear-covering member.

Ire other implementations, the wearable member is configured to be inserted into the subject's ear. For example, the wearable member includes at least one earphone or earbud and a pair of clip electrodes. Optionally, the pair of clip electrodes are configured to detachably couple to an external portion of the subject's ear or ears.

Alternatively or additionally, the sensor is an electroencephalography (EEG) sensor.

Alternatively or additionally, the plurality of electrodes are skin surface electrodes. For example, the plurality of electrodes are configured to contact the subject's ear canal and/or pinna region.

Alternatively or additionally, the plurality of electrodes include an active electrode, a reference electrode, and a ground electrode.

Alternatively or additionally, the controller is further configured to generate the stimulation signal.

Alternatively or additionally, the electrophysiological response signal is physiological activity of the subject's inner ear sensory epithelia.

Alternatively or additionally, the electrophysiological response signal comprises an early auditory potential. The early auditory potential includes at least one of the cochlear microphonic (CM) response, the auditory nerve neurophonic, the auditory nerve overlapped waveform, the summating potential of the cochlea, or the compound action potential.

Alternatively or additionally, the controller further includes an analog-to-digital converter (ADC) configured to convert the electrophysiological response signal into a digital signal.

Alternatively or additionally, the controller further includes a wireless transceiver. For example, the wireless transceiver is a low-power wireless transceiver.

Alternatively or additionally, the controller further includes signal conditioning circuitry.

Alternatively or additionally, the controller includes a microprocessor.

Alternatively or additionally, the device further includes a temperature sensor. In this implementation, the controller is optionally further configured to receive a temperature of the subject's skin from the temperature sensor.

A system for monitoring hearing sensitivity is also described herein. The system includes the device as described herein, and a computing device operably coupled to the controller of the device. The computing device includes a processor and a memory and is configured to receive, from the controller of the device, the electrophysiological response signal, and analyze the electrophysiological response signal.

Alternatively or additionally, the computing device is further configured to generate a warning in response to analyzing the electrophysiological response signal.

Alternatively or additionally, the step of analyzing the electrophysiological response signal includes converting the electrophysiological response signal into a frequency domain, and calculating a statistical measure of the frequency-domain electrophysiological response signal. Optionally, the statistical measure of the frequency-domain electrophysiological response signal is at least one of a mean, a standard deviation, a confidence interval, or a noise floor level.

Alternatively or additionally, the step of analyzing the electrophysiological response signal includes calculating a score based on the electrophysiological response signal. For example, the step of calculating the score includes comparing an amplitude measure of the electrophysiological response signal to a reference value, where the reference value is the subject's electrophysiological response at an earlier point in time, Optionally, the score is based on a difference between the amplitude measure of the electrophysiological response signal and the reference value. Alternatively or additionally, the amplitude measure is a normalized decibel power level of the electrophysiological response signal. Alternatively or additionally, the computing device is further configured to store the score. Alternatively or additionally, the computing device is further configured to generate display data comprising the score.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

DETAILED DESCRIPTION

Figure 1:
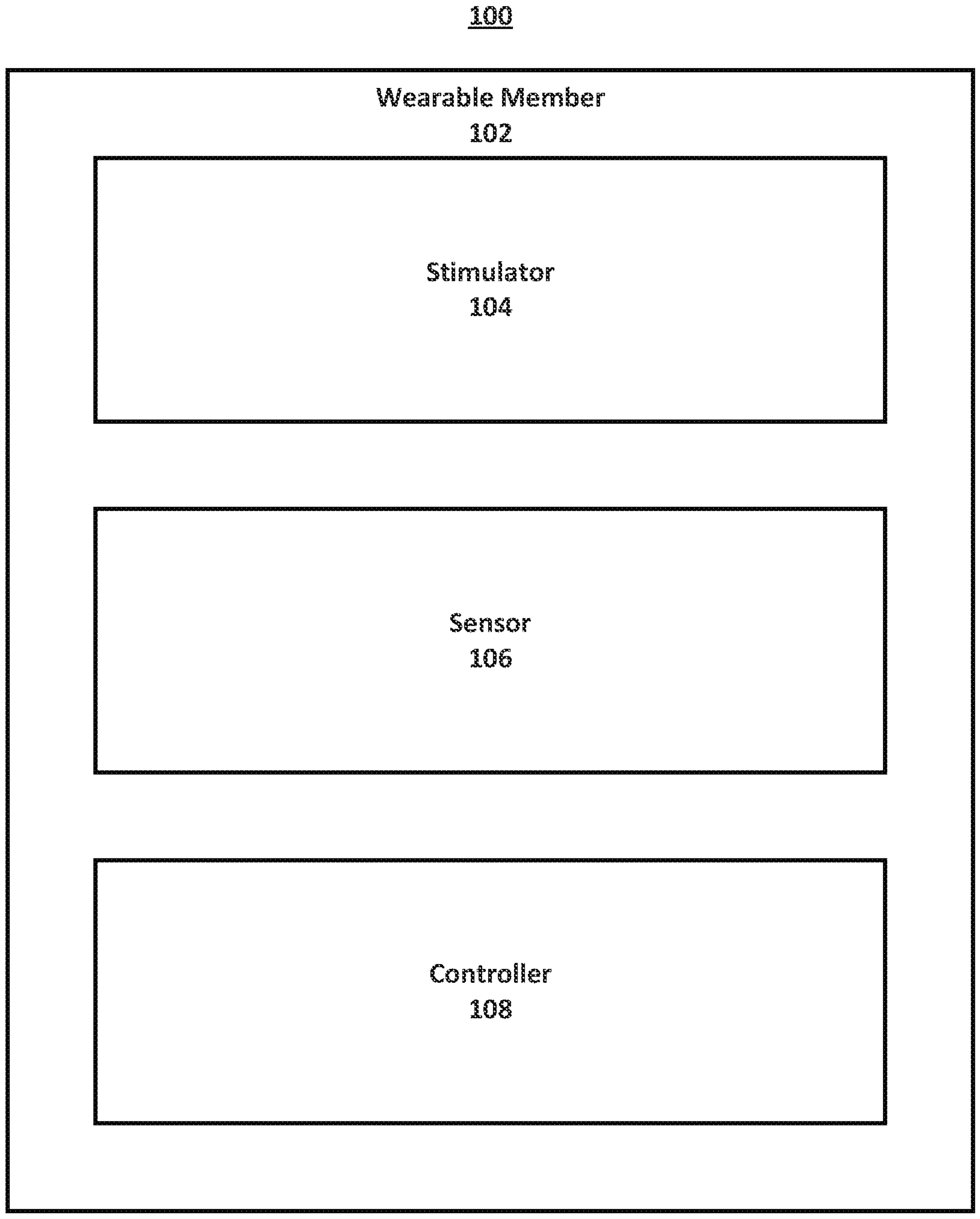
FIG. 1 is a block diagram of a portable device according to implementations described herein.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. While implementations will be described for objectively measuring the cochlear microphonic response of hair cells using a wearable device such as headphones, earphones, or earbuds, it will become evident to those skilled in the art that the implementations are not limited thereto, but are applicable for measuring other physiological response of the inner ear using the wearable device.

As used herein, the terms "about" or "approximately" when referring to a measurable value such as an amount, a percentage, and the like, is meant to encompass variations of ±20%, ±10%, ±5%, or ±1% from the measurable value.

The term "subject" or "user" is defined herein to include animals such as mammals, including, but not limited to, primates (e.g., humans), cows, sheep, goats, horses, dogs, cats, rabbits, rats, mice and the like. In some embodiments, the subject or user is a human.

Described herein are devices, systems, and methods for monitoring hearing sensitivity. These devices, systems, and methods allow users of headphones, earbuds, earphones, etc. quickly and objectively monitor hearing sensitivity to ensure safe listening habits. For example, a portable device is used to measure the physiology of the sensory cells (i.e. antenna) of the user's inner ear. In some implementations, the portable device is configured to deliver a tone (e.g., low frequency, suprathreshold level tone) to the user's ear. In other implementations, the portable device is configured to deliver bone conduction stimulation (e.g., low frequency, suprathreshold level tone) to the user's ear. In either implementation (i.e., acoustic or bone conduction stimulation), the portable device is configured to record the user's physiological response to stimulation from the sensory cells, e.g., the hair cells of the base of the cochlea. Changes in hearing sensitivity of the hair cells in this region, which is most sensitive to noise damage, results in decrease in the amplitude of the user's physiological response. It is therefore possible to monitor, and in some implementations continuously monitor, the user's hearing sensitivity over time. Hearing sensitivity monitoring can be performed over any period of time, e.g., days, weeks, months, years. Optionally, a hearing sensitivity index or score can be calculated using the user's monitored response, Additionally, data, warnings, instructions, and/or other information about hearing sensitivity (and loss thereof) can be provided to the user.

Referring now to FIG. 1, an example portable device 100 for monitoring hearing sensitivity is shown. The device 100 includes a wearable member 102, a stimulator 104, and a sensor 106. The stimulator 104 and the sensor 106 are integrated into the wearable member 102. In some implementations, the stimulator 104 is an electroacoustic transducer such as the speaker(s) found in conventional headphones, earbuds, earphones, etc. The electroacoustic transducer can deliver a tone (e.g., low frequency, suprathreshold level tone) to the subject's inner ear via the outer and/or middle ear. Example electroacoustic transducers are found in AIRPOD wireless earbuds from Apple, Inc. of Cupertino, California; GALAXY BUDS wireless earbuds from Samsung Electronics Co., Ltd, of Suwon-si, South Korea; and SOUNDLINK wireless headphones from Bose Corporation of Framingham, Massachusetts. It should be understood that above are provided only as example earbuds and headphones. Electroacoustic transducers are known in the art and therefore not described in further detail herein. Alternatively, in other implementations, the stimulator 104 is a bone oscillator, which is a mechanical device that is pushed out of an equilibrium position and vibrates back and forth at a given frequency. For bone conduction stimulation, the bone oscillator is placed in contact with a portion of the subject's skull (e.g., mastoid bone). When the bone oscillator is activated (i.e., vibrates), the bone conduction stimulation is transmitted directly to the subject's inner ear. Accordingly, the bone oscillator can deliver a tone (e.g., the low frequency, suprathreshold level tone) directly to the subject's cochlea, bypassing the outer and middle ear. An example bone oscillator is found in the B71 bone transducer headset from RadioEar of Middelfart, Denmark. It should be understood that above is provided only as an bone oscillator. Bone oscillators are known in the art and therefore not described in further detail herein.

Additionally, as described herein, the sensor 106 includes a plurality of electrodes. The electrodes can be made of a conductive material, e.g., a metal, alloy, ceramic, conductive rubber, conductive fabric, or other conductive material. The device 100 also includes a controller 108, which is operably coupled to the stimulator 104 and the sensor 106. The controller 108 can be coupled to the stimulator 104 and/or sensor 106 through one or more communication links. This disclosure contemplates the communication links are any suitable communication link. For example, a communication link may be implemented by any medium that facilitates data exchange including, but not limited to, wired, wireless and optical links. Optionally, in some implementations, the controller 108 is integrated into the wearable member 102.

Figure 2:
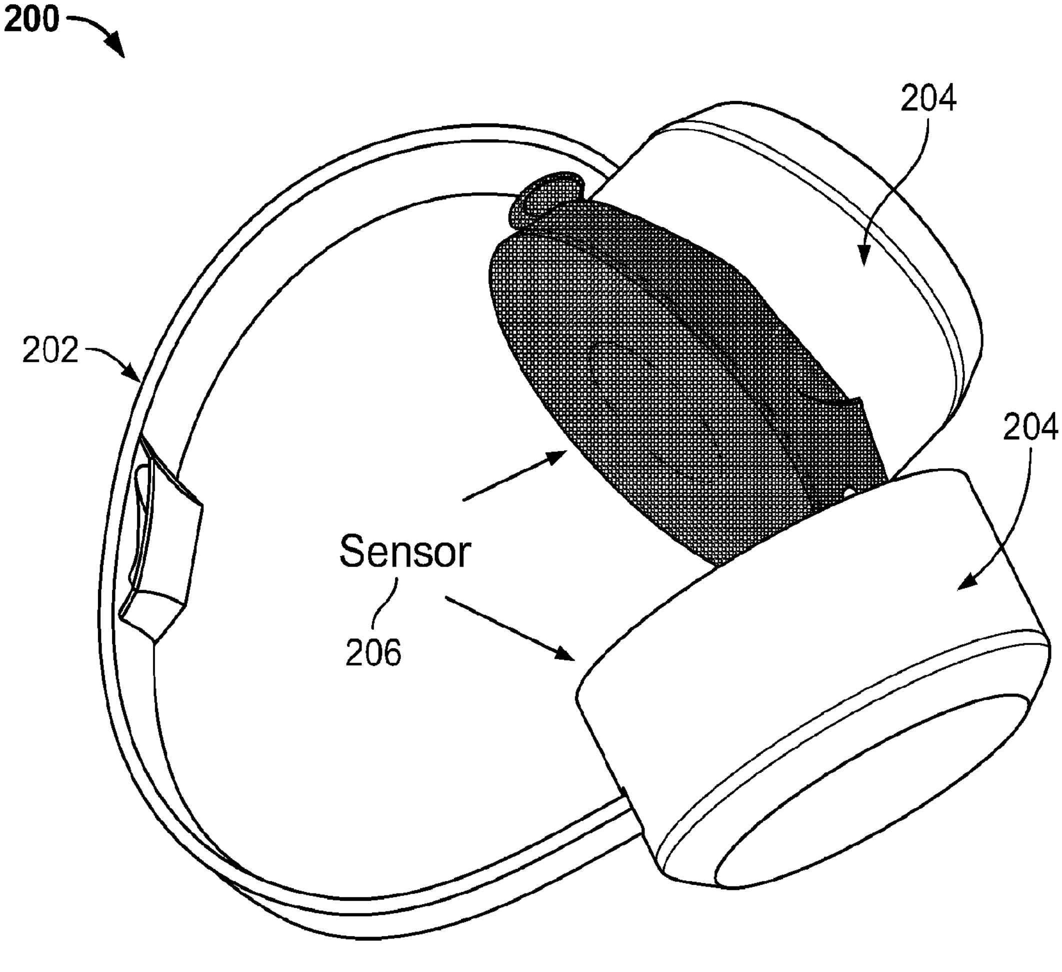
FIG. 2 is an image showing headphones according to implementations described herein.

Referring now to FIG. 2, example headphones 200 are shown. This disclosure contemplates that the portable device 100 of FIG. 1 can optionally be a set of headphones. Headphones are designed to be worn on or around the head of a user (also referred to herein as "subject"). For example, headphones 200 can include one or more (e.g., typically two) ear-covering members, which are connected by a band that is designed to extend around a portion of the user's head. In some implementations, the band is designed to extend around the top of the user's head. In other implementations, the headphones may be circum-aural where the band is designed to extend around the back of the user's head. It should be understood that the band and ear-covering members are a "wearable member" as described herein. Additionally, although the headphones 200 in FIG. 2 include two ear-covering members, this disclosure contemplates that the headphones 200 may include a different number of ear-covering members (e.g., a single ear-covering member) in other implementations. Headphones are well known in the art and their configuration is not described in further detail herein. This disclosure contemplates that the stimulator (e.g., electroacoustic transducer), sensor, and/or controller described herein can be integrated into any headphones known in the art. Such headphones may be wired or wireless devices. As shown in FIG. 2, the headphones 200 include a wearable member 202, an electroacoustic transducer 204, and a sensor 206. The electroacoustic transducer 204 and the sensor 206 are integrated into the wearable member 202. Optionally, as shown in FIG. 2, the ear-covering member of the headphones 200 serves as the sensor 206 (e.g., an EEG sensor). In this implementation, the ear-covering member is made of a conductive material and used to record the electrophysiological response to acoustic stimulation.

Figure 3:
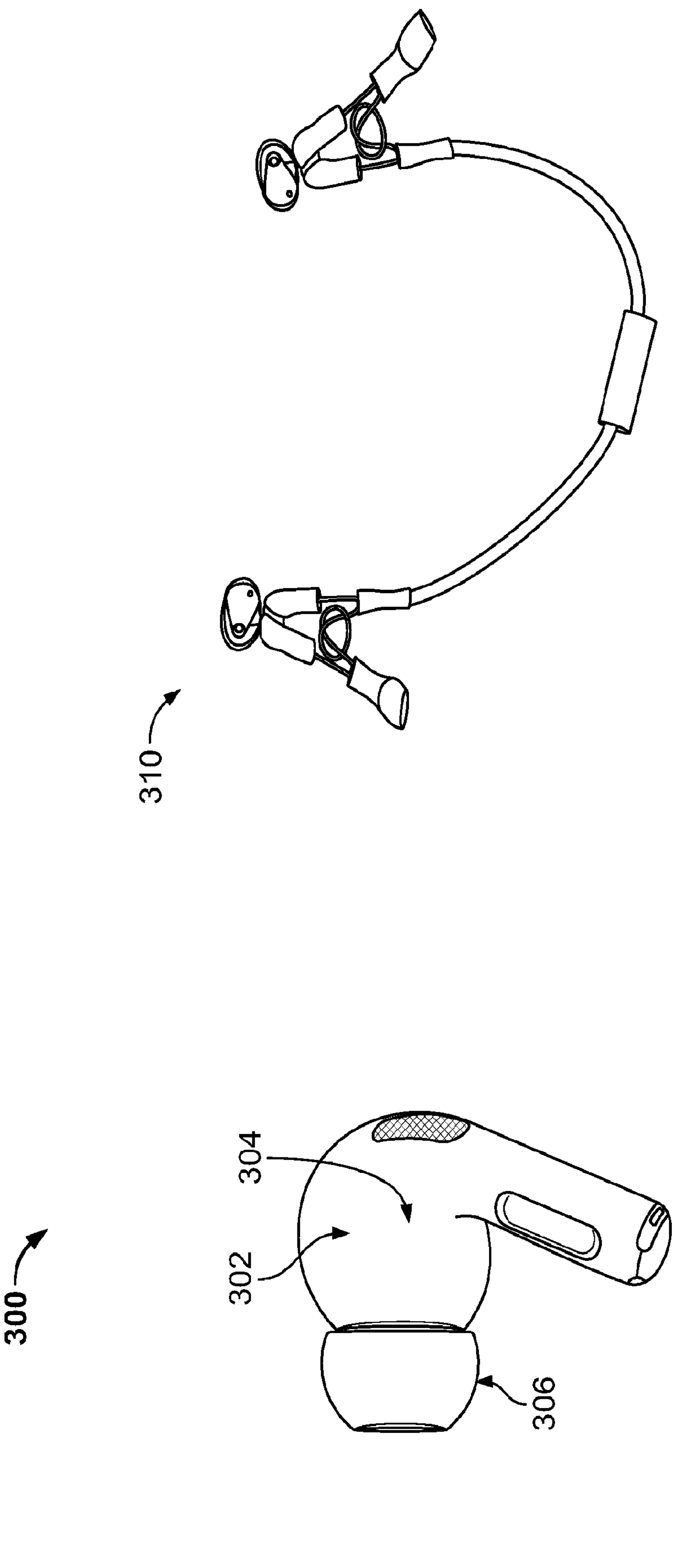
FIG. 3 is an image showing earbuds according to implementations described herein.

Referring now to FIG. 3, example earbuds 300 are shown. This disclosure contemplates that the portable device 100 of FIG. 1 can optionally be a set of earbuds (shown in FIG. 3) or earphones (not shown). Earbuds and earphones are designed to be inserted into a user's ear. As used herein, earbuds include cushions (e.g., plastic, foam, silicone, rubber, fabric etc.) that are designed to fit within the user's ear canal, and earphones are designed to fit outside of the user's ear canal. Although earbuds 300 are shown in FIG. 3, this disclosure contemplates that the portable device described herein can be earphones. Earbuds 300 can include one or more (e.g., typically two) members designed to insert into the user's ears. It should be understood that the earbuds/earphones are a "wearable member" as described herein. Additionally, although the earbuds 300 in FIG. 3 includes a single member, this disclosure contemplates that the earbuds 300 may include a different number of members (e.g., two members) in other implementations. Earbuds/earphones are well known in the art and their configuration is not described in further detail herein. This disclosure contemplates that the stimulator (e.g., electroacoustic transducer), sensor, and/or controller described herein can be integrated into any earbuds/earphones known in the art, Such earbuds/earphones may be wired or wireless devices. As shown in FIG. 3, the earbuds 300 include a wearable member 302, an electroacoustic transducer 304, and a sensor 306. The electroacoustic transducer 304 and the sensor 306 are integrated into the wearable member 302, Additionally, in the earbud/earphone implementations, the portable device also includes a pair of clip electrodes 310. Optionally, the pair of clip electrodes 310 are configured to detachably couple to an external portion of the user's ear or ears. This disclosure contemplates that the pair of clip electrodes 310 can serve as the reference and/or or ground electrodes (described in further detail below). In contrast to headphones (which include a relatively larger wearable member), the pair of clip electrodes 310 is a separate element that is needed to provide a reference and/or or ground, i.e., one physically distant from the sensor 306 that is integral with the wearable member 302.

Referring again to FIG. 1, the sensor 106 is configured to record the user's electrophysiological response to stimulation. As described above, the stimulation is acoustic stimulation or bone conduction stimulation. In either case, the stimulation elicits the same electrophysiological response in the user. Optionally, in some implementations, the sensor 106 is an electroencephalography (EEG) sensor. For example, the plurality of electrodes of the sensor 106 can be skin surface electrodes that are configured to contact the subject's ear canal and/or pinna region. In these implementations, the plurality of electrodes include an active electrode, a reference electrode, and a ground electrode. In some implementation, impedance measurements taken with the sensor 106 are used to check whether the sensor 106 is in contact with the user's skin. It should be understood that an EEG sensor is provided only as an example. This disclosure contemplates that the sensor 106 can be a different type of sensor capable of detecting the user's electrophysiological response to stimuli. Alternatively or additionally, this disclosure contemplates that the device 100 can include other sensors. For example, the device 100 can optionally further include a temperature sensor that is capable of measuring a temperature of the user's skin. The temperature sensor can be integrated with or separate from the sensor 106. Measured temperature can be used to determine optimal placement for the sensor 106. Accordingly, the device 100 can be configured to ensure skin impedances are appropriate and also use temperature readings to gauge if the sensor 106 is making full surface area contact with the skin. Optionally, optimal electrode placemen when temperature readings are between 95-100 degrees Fahrenheit on all electrodes of the sensor 106.

As described herein, the controller 108 is configured to actuate the stimulator 104 to deliver a stimulation signal to the user's ear. When the stimulator 104 is an electroacoustic transducer, the acoustic stimulation signal (e.g., low frequency, suprathreshold level tone) is delivered to the user's inner ear via the outer and/or middle ear. When the stimulator 104 is a bone oscillator, the bone conduction stimulation (e.g., low frequency, suprathreshold level tone) is delivered directly to the user's inner ear, bypassing the outer and middle ear. It should be understood that headphones, earbuds, and earphones include speakers (e.g., electroacoustic transducers) capable of delivering such a stimulation signal. Alternatively, it should be understood that a wearable device with integrated bone oscillator is capable of delivering such a stimulation signal. Optionally, the controller 108 is further configured to generate the stimulation signal. When the stimulator 104 is an electroacoustic transducer, the controller 108 generates the acoustic stimulation signal and actuates the stimulator to deliver stimulation to the user's ear. When the stimulator 104 is a bone oscillator, the controller 108 actuates the bone oscillator to generate and deliver the bone conduction stimulation to the user's ear. The controller 108 is also configured to receive an electrophysiological response signal of the user in response to the stimulation. Such electrophysiological response is recorded by the sensor 106. In other words, the acoustically generated sounds or bone conduction stimulation (i.e. the stimulation signal) activates the user's inner ear, and electrical fields associated with such activity are detectable by the sensor 106, which is located in, on, or near the user's inner ear.

Figure 4:
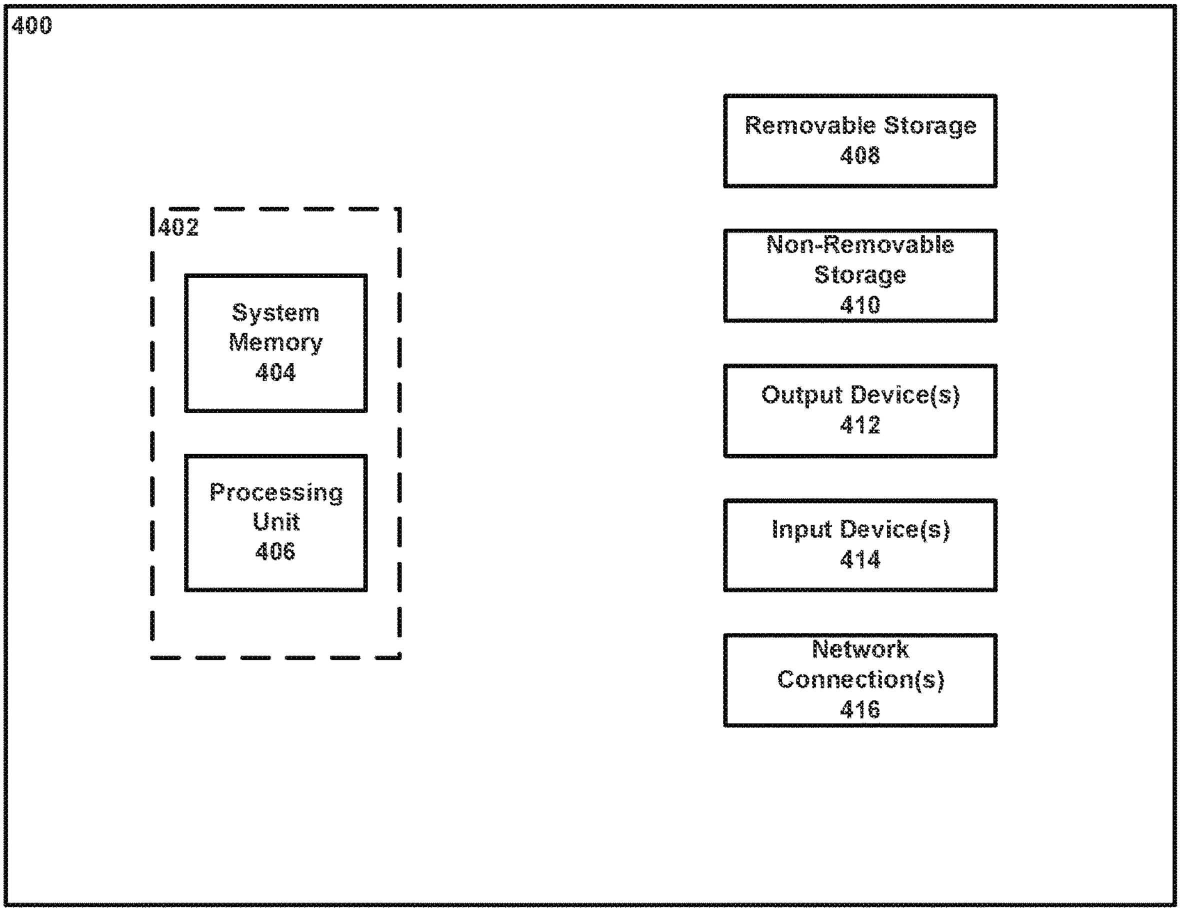
FIG. 4 is an example computing device.

The controller can include a microprocessor (e.g., at least a processor and memory such as shown by dashed line 402 in FIG. 4). Alternatively or additionally, the controller 108 further includes an analog-to-digital converter (ADC) configured to convert the electrophysiological response signal into a digital signal. Alternatively or additionally, the controller 108 further includes a wireless transceiver, for example, to wirelessly receive and/or transmit the electrophysiological response signal. The wireless transceiver is optionally a low-power wireless transceiver. Low-power wireless transceivers include, but are not limited to, transceivers configured to implement the BLUETOOTH wireless technology standard. Alternatively or additionally, the controller 108 further includes signal conditioning circuitry, which can include, but is not limited to, operational amplifiers, instrumentation amplifiers, resistors, capacitors, or other electrical components. Alternatively or additionally, the device 100 can further include a battery or other energy source, which is optionally integrated into the wearable member 102.

The stimulation signal described herein is configured to activate the user's inner ear. This disclosure contemplates that the stimulus signal can include a single frequency tone or multiple frequency tones (e.g. frequency modulated, or phonemes/words). Alternatively or additionally, the stimulus signal can be delivered at a single loudness level or the loudness level can be modulated (amplitude modulated). This disclosure also contemplates that the stimulation can be of brief duration, e.g., from a very short duration such as 10 microseconds (μsec) to longer durations such as 1,000-5,000 milliseconds or longer. It should be understood that the durations above are provided only as examples and can have other values. Alternatively or additionally, the stimulation signal can be delivered at a loudness (intensity) level that is measured in decibels (dB) of sound pressure level (SPL) that can range from 0-130 dB SPL. It should be understood that the intensity levels above are provided only as examples and can have other values.

The electrophysiological response signal described herein is physiological activity of the subject's inner ear sensory epithelia. It is induced by the stimulation signal described herein and detected by the sensor 106. The electrophysiological response signal can include an early auditory potential. The early auditory potential includes at least one of the cochlear microphonic (CM) response, the auditory nerve neurophonic, the auditory nerve overlapped waveform, the summating potential of the cochlea, or the compound action potential. This disclosure contemplates performing a signal analysis on the electrophysiological response signal to identify and/or isolate one or more of the above components. Alternatively or additionally, this disclosure contemplates using one or more of the above components to calculate a score (also referred to herein as "index," "hearing index," or "hearing index score"). The score can be used to continuously monitor the user's hearing sensitivity (e.g., as shown by reference number 506 in FIG. 5) over a period of time (e.g., days, weeks, months, years, or any other time interval).

The portable device 100 can optionally be operably coupled to a computing device (e.g., computing device 400 of FIG. 4). The device 100 can be coupled to the computing device through one or more communication links. This disclosure contemplates the communication links are any suitable communication link. For example, a communication link may be implemented by any medium that facilitates data exchange between the device 100 and computing device including, but not limited to, wired, wireless and optical links. Example communication links include, but are not limited to, a local area network (LAN), a wireless local area network (WLAN), a wide area network (WAN), a metropolitan area network (MAN), Ethernet, the Internet, or any other wired or wireless link such as WiFi, WiMax, 3G, 4G, or 5G. In some implementations, the computing device is a smartphone or tablet computer, and the portable device 100 is operably coupled to the computing device via a wireless transceiver (described above) or wired link. It should be understood that a smartphone and tablet are provided only as an example. This disclosure contemplates that the device 100 can be operably coupled to other types of computing devices.

Figure 5:
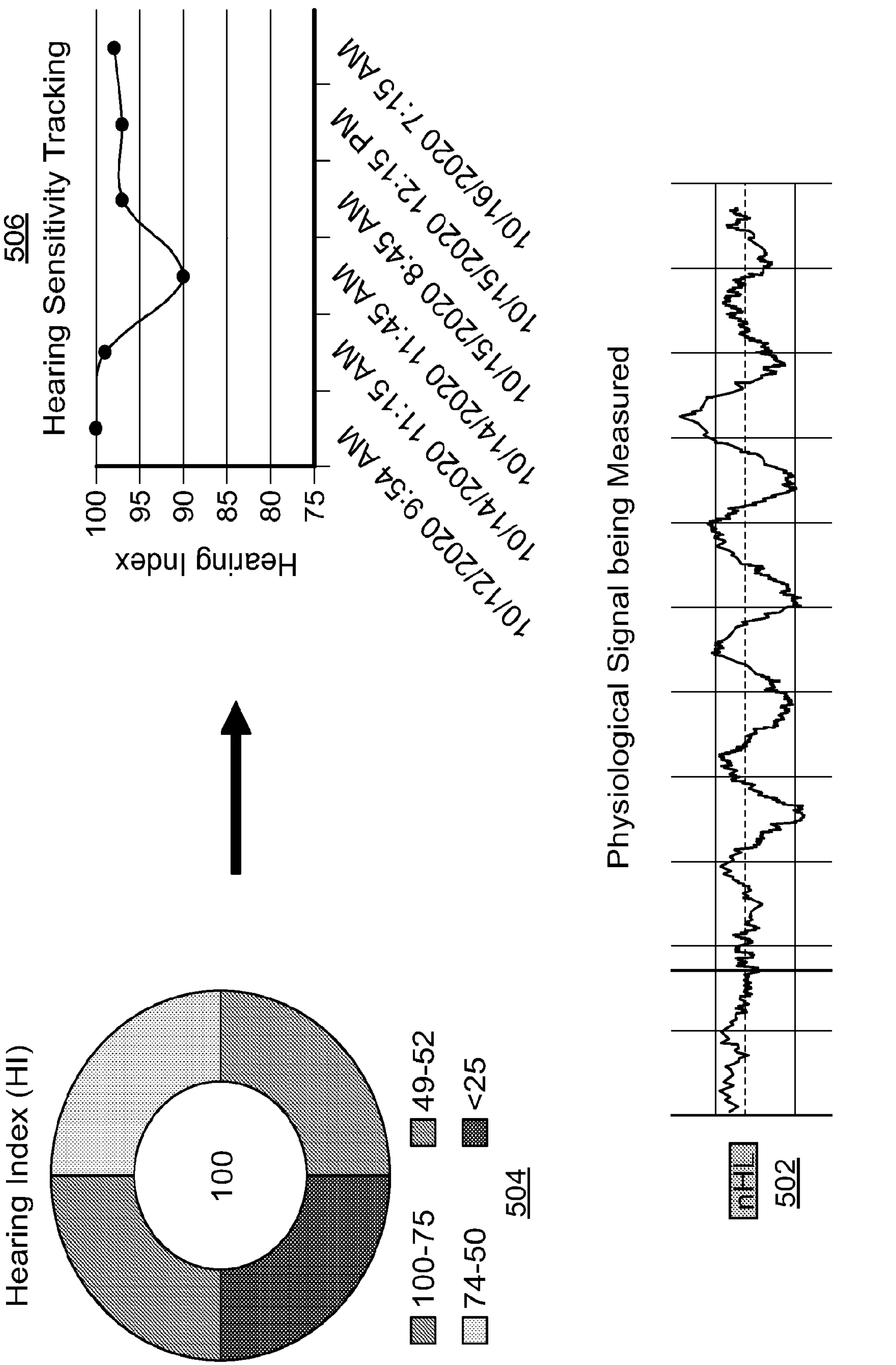
FIG. 5 illustrates hearing sensitivity tracking according to implementations described herein.

Referring now to FIG. 5, the computing device can be configured to receive the electrophysiological response signal 502. The computing device can also be configured to analyze the electrophysiological response signal. In some implementations, the step of analyzing the electrophysiological response signal includes converting the electrophysiological response signal into a frequency domain (e.g., using fast Fourier transform), and calculating a statistical measure of the frequency-domain electrophysiological response signal. Optionally, the statistical measure of the frequency-domain electrophysiological response signal is at least one of a mean, a standard deviation, a confidence interval, or a noise floor level.

Alternatively or additionally, the step of analyzing the electrophysiological response signal includes calculating a score 504 based on the electrophysiological response signal. For example, the step of calculating the score includes comparing an amplitude measure of the electrophysiological response signal to a reference value, where the reference value is the subject's electrophysiological response at an earlier point in time. Optionally, the score is based on a difference between the amplitude measure of the electrophysiological response signal and the reference value. Alternatively or additionally, the amplitude measure is a normalized decibel power level of the electrophysiological response signal.

Alternatively or additionally, the computing device can optionally be further configured to store the hearing score.

Alternatively or additionally, the computing device can optionally be further configured to generate display data for the score. The display can optionally be a color wheel 504 with the score displayed in the middle. The user can view a tracking graph display (e.g., reference number 506 of FIG. 5) the score over time (time/date stamped), The user can select the length of time over which to view the score (e.g. one week, monthly, yearly, etc.).

Alternatively or additionally; the computing device can optionally be configured to generate a warning in response to analyzing the electrophysiological response signal. For example, if a change in hearing sensitivity greater than or equal to a threshold (e.g., 50% of initialization value), a warning can be generated (e.g., "Significant changes in hearing sensitivity have been detected") and displayed to the user.

Figure 6:
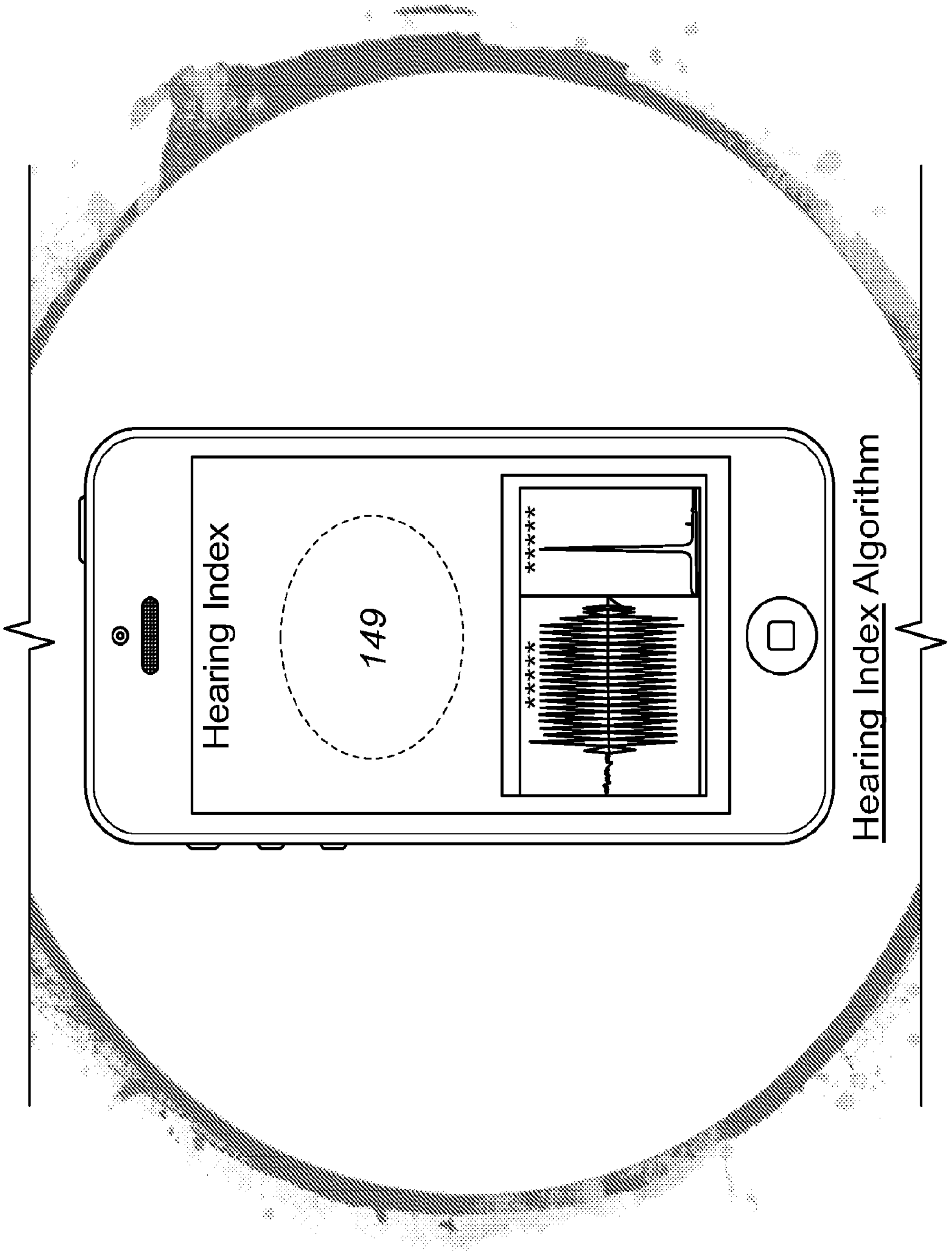
FIG. 6 illustrates display of hearing index score on a mobile device according to implementations described herein.

Referring now to FIG. 6, an example display of hearing index score on a mobile device is shown. This disclosure contemplates that the user can execute a program (e.g., mobile app or other application program) or access a web page to display a user interface. The user can optionally enter demographic information and select a test with the user interface. For example, the user may select an initial hearing measurement test. This test is configured to deliver an acoustic stimulus signal to the user and record the user's initial response to the same with a device (e.g., device 100 of FIG. 1). This measurement serves as a baseline or initialization value. Thereafter, the user may begin to monitor hearing sensitivity. Again, this test is configured to deliver an acoustic stimulus signal to the user and record the user's subsequent response to the same with a device (e.g., device 100 of FIG. 1). The subsequent response can be used to calculate a hearing index (e.g., the score described herein) by comparison to the baseline.

An example hearing index (e.g., the score described herein) algorithm is as follows:

- the amplitude of the physiological response obtained from the ear level sensor in microvolts (uV),
- this amplitude is converted to decibels (dB) by: $20*\log_{10}$ (uV), and
- the dB signal is then normalized to 1 and multiplied by 100: dB/dB*100%.

For subsequent trials, every time the user measures the physiological response, the response is analyzed and referenced to the value (dB) obtained at the initialization phase.

The reference calculation is as follows:

$$20*\text{Log}_{10}(\text{current value/initialization value})$$

Hearing indices are determined by the amount difference in dB between the Initialization value and the current value. If values are less than 1/2 of the baseline value, then for every dB difference (below initialization dB value) there is a 3% subtraction in Hearing Index value. If values are greater than 1/2 change lower than Initialization value, there is a 50% subtraction in hearing index value and a 3% change for every dB thereafter.

It should be understood that the hearing index algorithms described above are provided only as examples. This disclosure contemplates calculating the hearing index using other algorithms.

It should be appreciated that the logical operations described herein with respect to the various figures may be implemented (1) as a sequence of computer implemented acts or program modules (i.e., software) running on a computing device (e.g., the computing device described FIG. 4), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Referring to FIG. 4, an example computing device 400 upon which the methods described herein may be implemented is illustrated. It should be understood that the example computing device 400 is only one example of a suitable computing environment upon which the methods described herein may be implemented. Optionally, the computing device 400 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In its most basic configuration, computing device 400 typically includes at least one processing unit 406 and system memory 404. Depending on the exact configuration and type of computing device, system memory 404 may be volatile (such as random access memory (RAM)), non-volatile (such as read-only memory (ROM), flash memory, etc.), or some combination of the two. This most basic configuration is illustrated in FIG. 4 by dashed line 402. The processing unit 406 may be a standard programmable processor that performs arithmetic and logic operations necessary for operatic n of the computing device 400. The computing device 400 may also include a bus or other communication mechanism for communicating information among various components of the computing device 400.

Computing device 400 may have additional features/functionality. For example, computing device 400 may include additional storage such as removable storage 408 and non-removable storage 410 including, but not limited to, magnetic or optical disks or tapes. Computing device 400 may also contain network connection(s) 416 that allow the device to communicate with other devices. Computing device 400 may also have input device(s) 414 such as a keyboard, mouse, touch screen, etc. Output device(s) 412 such as a display, speakers, printer, etc. may also be included. The additional devices may be connected to the bus in order to facilitate communication of data among the components of the computing device 400. All these devices are well known in the art and need not be discussed at length here.

The processing unit 406 may be configured to execute program code encoded in tangible, computer-readable media. Tangible, computer-readable media refers to any media that is capable of providing data that causes the computing device 400 (i.e., a machine) to operate in a particular fashion. Various computer-readable media may be utilized to provide instructions to the processing unit 406 for execution. Example tangible, computer-readable media may include, but is not limited to, volatile media, non-volatile media, removable media and non-removable media implemented in any method or technology for storage of information such as computer readable instructions, data structures, program modules or other data. System memory 404, removable storage 408, and non-removable storage 410 are all examples of tangible, computer storage media, Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 406 may execute program code stored in the system memory 404. For example, the bus may carry data to the system memory 404, from which the processing unit 406 receives and executes instructions. The data received by the system memory 404 may optionally be stored on the removable storage 408 or the non-removable storage 410 before or after execution by the processing unit 406.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The hEar! System is a wireless headphone that can be used by general consumers to listen to music, with three built-in EEG sensors that comprise the earpieces and headband. Additionally, the software application on a smartphone controls stimulus delivery, and collection and processing of electrophysiological activity of the inner ear, permitting the end user to measure and track their hearing sensitivity over time using proprietary algorithms (i.e., Hearing Index/Score). Currently, no system exists that runs via a smartphone using a consumer headphone to objectively measure inner ear physiology. The approach described herein is quick, taking less than 1 minute to conduct. We have studied this type of measurement for several years and its relation to inner ear trauma using more invasive and bulky setups in humans. This has provided the foundational science for this product and has allowed us to understand the biological signal of interest and the best approach to analyzing it. The hEar! System takes the scientific findings gleaned from previous work and implements them into a consumer product that is easy to use, is functional, and empowers the user with his/her own hearing health data.

Currently, there is no objective solution/product which exists on the market, outside of a person visiting a licensed healthcare provider to have a hearing exam conducted (status quo), However, subjective solutions/products for screening hearing sensitivity which do not require a visit to a licensed healthcare provider do exist which comprise a software application on a smart device. These types of products require the user to listen to audible sounds in a quiet room and respond "yes" or "no" to indicate if they heard a sound. This approach takes approximately 10 minutes and requires user input, while not measuring any actual biological activity. In contrast, the hEar! System is entirely objective (measures the biological activity of the hearing organ), requires no user feedback, can be completed in less than one minute, and does not require a completely silent room to be performed. This system allows for screening and tracking of the user's hearing sensitivity over time (repeated measurements) and can alert the end user when listening habits have become unsafe in regards to noise level based on physiology of the ear.

Although the subject matter has been described in language specific to structural features and/or methodological acts, it is to be understood that the subject matter defined in the appended claims is not necessarily limited to the specific features or acts described above. Rather, the specific features and acts t escribed above are disclosed as example forms of implementing the claims.

What is claimed:

1. A system for monitoring hearing sensitivity, the system comprising:

a portable device that comprises:

- a wearable member audio used to deliver user-selected playback audio;
- a stimulator integrated into the wearable member;
- a sensor integrated into the wearable member, the sensor comprising a plurality of electrodes that are configured to optimize recording of cochlear microphonic and related early auditory potentials from the ear canal/pinna region; and
- a controller operably coupled to the stimulator and the sensor, the controller being configured to:

deliver a stimulation signal to a subject's ear using the stimulator that is delivered with the user-selected playback audio; and receive an electrophysiological response signal of the subject in response to the stimulation signal, the electrophysiological response signal being recorded by the sensor, wherein the electrophysiological response signal comprises an early auditory potential from inner-ear sensory epithelia; and a computing device operably coupled to the controller of the device, the computing device comprising a processor and a memory, the memory having computer-executable instructions stored thereon that, when executed by the processor, cause the processor to:

receive, from the controller of the device, the electrophysiological response signal; and analyze the electrophysiological response signal, wherein analyzing the electrophysiological response signal comprises calculating a score based on the electrophysiological response signal, wherein calculating the score comprises comparing an amplitude measure of the electrophysiological response signal to a reference value, wherein the reference value is the subject's electrophysiological response at an earlier point in time, and wherein the amplitude measure is a normalized decibel power level of the electrophysiological response signal.

2. The system of claim 1, wherein the wearable member is configured to be worn around a portion of the subject's head, the wearable member comprising at least one ear-covering member.

3. The system of claim 1, wherein the wearable member is configured to be inserted into the subject's ear, the wearable member comprising at least one earphone or earbud, and a pair of clip electrodes.

4. The system of claim 3, wherein the pair of clip electrodes are configured to detachably couple to an external portion of the subject's ear or ears.

5. The system of claim 1, wherein the sensor is an electroencephalography (EEG) sensor.

6. The system of claim 1, wherein the plurality of electrodes are skin surface electrodes.

7. The system of claim 6, wherein the plurality of electrodes are configured to contact the subject's ear canal and/or pinna region.

8. The system of claim 1, wherein the plurality of electrodes comprise an active electrode, a reference electrode, and a ground electrode.

9. The system of claim 1, wherein the controller is further configured to generate the stimulation signal.

10. The system of claim 1, wherein the early auditory potential comprises at least one of a cochlear microphonic (CM) response, an auditory nerve neurophonic, an auditory nerve overlapped waveform, a summating potential of the cochlea, or a compound action potential.

11. The system of claim 1, wherein the controller further comprises an analog-to-digital converter (ADC) configured to convert the electrophysiological response signal into a digital signal.

12. The system of claim 1, wherein the controller further comprises a wireless transceiver.

13. The system of claim 12, wherein the wireless transceiver is a low-power wireless transceiver.

14. The system of claim 1, wherein the controller further comprises signal conditioning circuity.

15. The system of claim 1, wherein the controller comprises a microprocessor.

16. The system of claim 1, further comprising a temperature sensor, wherein the controller is further configured to receive a temperature of the subject's skin from the temperature sensor.

17. The system of claim 1, wherein the controller is integrated into the wearable member.

18. The system of claim 1, wherein the stimulator is an electroacoustic transducer and the stimulation signal is an acoustic stimulation signal, the controller being configured to actuate the electroacoustic transducer to deliver the acoustic stimulation signal to the subject's ear.

19. The system of claim 18, wherein the acoustic stimulation signal is configured to activate the subject's inner ear.

20. The system of claim 1, wherein the stimulator is a bone oscillator and the stimulation signal is a bone conduction stimulation, the controller being configured to actuate the bone oscillator to deliver the bone conduction stimulation to the subject's ear.

21. The system of claim 20, wherein the bone conduction stimulation is configured to activate the subject's inner ear.

22. The system of claim 1, wherein the memory has further computer-executable instructions stored thereon that, when executed by the processor, cause the processor to generate a warning in response to analyzing the electrophysiological response signal.

23. The system of claim 1, wherein analyzing the electrophysiological response signal comprises:

converting the electrophysiological response signal into a frequency domain; and calculating a statistical measure of the frequency-domain electrophysiological response signal.

24. The system of claim 23, wherein the statistical measure of the frequency-domain electrophysiological response signal is at least one of a mean, a standard deviation, a confidence interval, or a noise floor level.

25. The system of claim 1, wherein the score is based on a difference between the amplitude measure of the electrophysiological response signal and the reference value.

26. The system of claim 1, wherein the memory has further computer-executable instructions stored thereon that, when executed by the processor, cause the processor to store the score.

27. The system of claim 1, wherein the memory has further computer-executable instructions stored thereon that, when executed by the processor, cause the processor to generate display data comprising the score.

* * * * *